Figure 1:
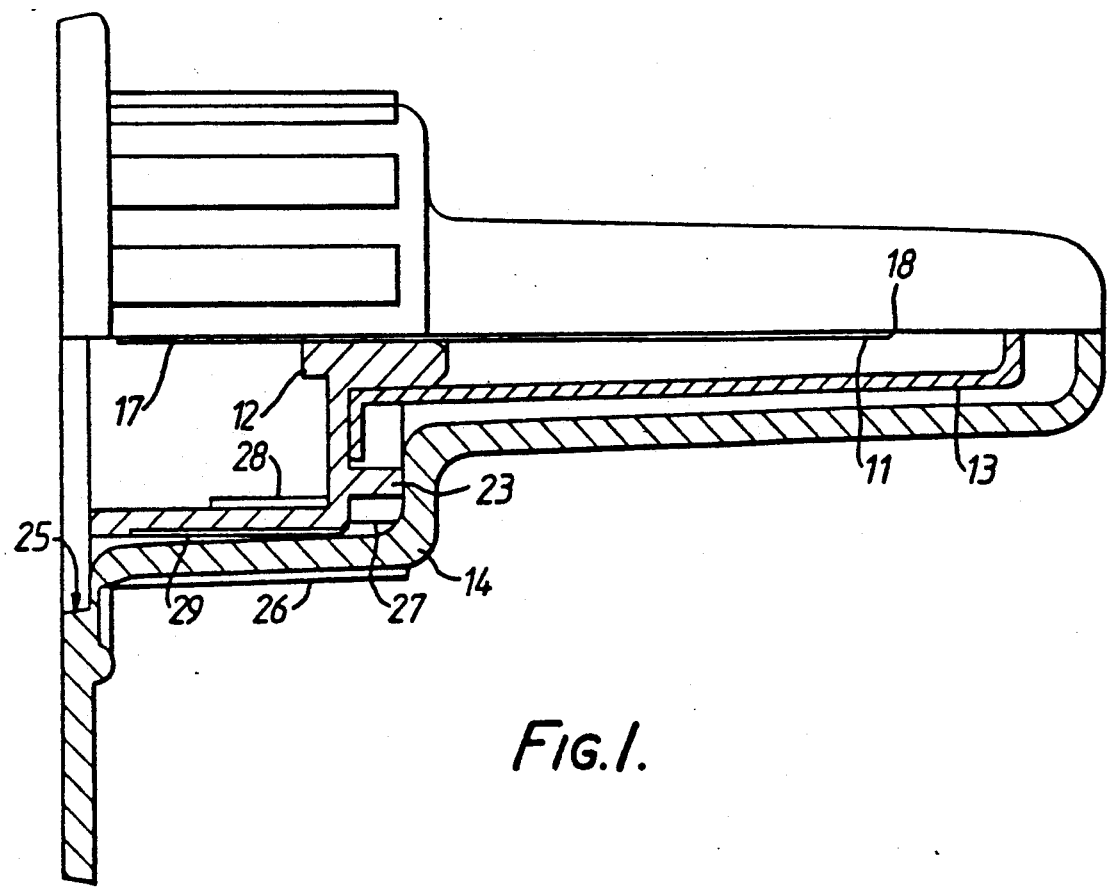

United States Patent [19]

Crossman

[11] Patent Number: 5,015,235

[45] Date of Patent: May 14, 1991

[54] SYRINGE NEEDLE COMBINATION

[75] Inventor: David D. Crossman, Watlington, England

[73] Assignee: National Carpet Equipment, Inc., Maple Grove, Minn.

[21] Appl. No.: 408,438

[22] Filed: Sep. 15, 1989

Related U.S. Application Data

[63] Continuation of Ser. No. 153,066, Feb. 8, 1988, abandoned.

[30] Foreign Application Priority Data

Feb. 20, 1987 [GB] United Kingdom ............... 870427

[51] Int. Cl.⁵ ............................................. A61M 5/00
[52] U.S. Cl. ...................................... 604/117; 604/187
[58] Field of Search ............... 604/187, 192, 197, 178, 604/117, 263

[56] References Cited

U.S. PATENT DOCUMENTS 1,592,462  7/1926  MacGregor .................... 604/192
1,711,594  5/1929  Gillespie ......................... 206/365
2,117,469  5/1938  Woodyatt ......................... 206/365
4,022,191  5/1977  Jamshidi .......................... 604/117
4,430,080  2/1984  Pasquini et al. ................. 604/263
4,735,311  4/1988  Lowe et al. ...................... 206/365
4,795,432  1/1989  Karczmer ........................ 604/263
4,804,371  2/1989  Vaillancourt .................... 604/263
4,816,022  3/1989  Poncy .............................. 604/198

Primary Examiner—William E. Kamm
Assistant Examiner—Scott M. Getzow
Attorney, Agent, or Firm—Haugen and Nikolai

[57] ABSTRACT

A needle (11) for a hypodermic syringe is a force fit on a hub (12) which can be secured onto a container for the fluid to be injected. A cover (13) fits over a boss on the hub and provides an enclosure for the needle. The assembly of hub, needle and cover are housed in a container (14) which fits around the hub (12). To control the depth of penetration of the needle, the user selects an adjuster (15) from a set of adjusters of different sizes and fits it over a part of the hub.

5 Claims, 1 Drawing Sheet

SYRINGE NEEDLE COMBINATION

This application is a continuation of application Ser. No. 153,066, filed Feb. 8, 1988, now abandoned.

This invention relates to needles for hypodermic syringes and other injection devices. It is usual for a needle to be supplied in its individual container so that it can be fitted to a syringe for use and then replaced in a container and disposed of in the container after use to avoid spreading contamination. With such an arrangement of a needle in a container for fitting to a syringe, it is not easy to provide means for controlling the depth to which the needle can be inserted in a patient, and an object of the present invention is to provide a simple method of enabling that to be achieved.

According to the present invention a syringe needle combination includes a needle for a syringe, a hub carrying the needle, and a depth adjuster arranged to be fitted to the hub to set the degree of penetration of the needle in a patient.

Insertion might be into subcutaneous or intramuscular regions, or into a vein, and depending on the location, the degree of penetration needs to be selected within a wide range.

The needle will in general be a tight fit in the hub; the hub is itself adapted for fitting over the end of a syringe. If it is a double-ended needle, one end will then penetrate a cover over a cartridge in the syringe which contains the fluid to be injected. With a single-ended needle, the end of the needle in the hub will be merely positioned to receive fluid ejected from the syringe.

The depth adjuster can be arranged for simple friction fitting over a portion of the hub and, preferably, there are a number of alternative depth adjusters of different lengths so that the user can select which adjuster to fit over the hub in dependence on the depth to which the needle is to penetrate.

A preferred form of depth adjuster is that of a sleeve which will be spaced around the needle when fitted to the hub and will extend from the hub by a desired amount in dependence on the depth to which the needle is to penetrate.

Figure 2:
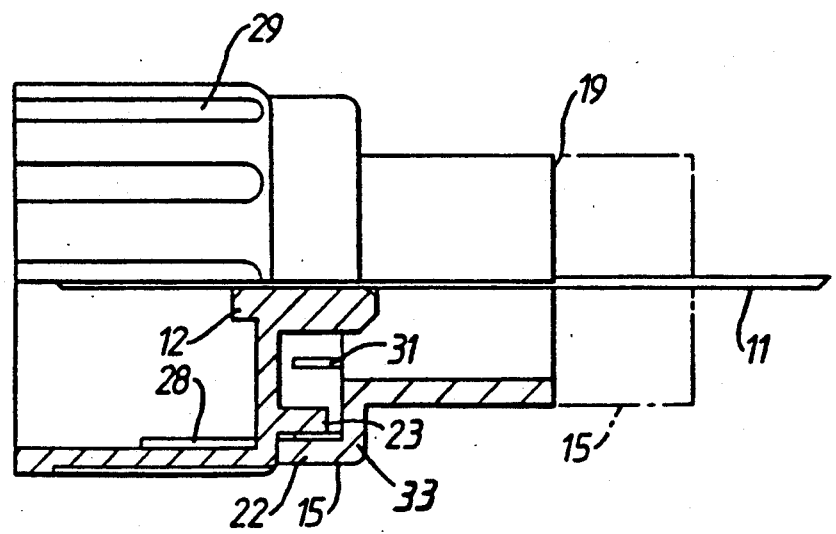

The invention may be carried into practice in various ways, and one embodiment will now be described by way of example with reference to the accompanying drawings, in which:

FIG. 1 is an elevation, partly in cross-section, of an assembly of a double-ended hypodermic syringe needle and case as supplied; and FIG. 2 shows the needle of FIG. 1 when ready for use.

The needle 11 is made from stainless steel tube and is firmly bonded in a central bore in a needle hub 12 moulded from translucent polypropylene. The exposed end of the needle 11 is covered when not in use by a polythene needle cover 13 which is a tight fit on a boss formed on the hub 12. As supplied, the assembly of the needle, the hub and the cover is positioned within a container 14 moulded from polystyrene.

The assembly of FIG. 1 is supplied with alternative depth adjusters 15 of moulded polypropylene shown in use in FIG. 2.

After removal of the hub and needle assembly and the cover from the container 14, the hub can be screwed over an end of the container of the liquid (not shown) to be injected by the syringe and the lefthand end 17 of the needle penetrates the closure of the fluid container.

When the cover 13 is removed, the right hand end, or exposed end 18 of the needle can be inserted in a patient so that, by operation of the syringe, the fluid can be injected.

In the example being described, the needle 11 projects 12.5 mm from the end of the hub 12 and it is not easy to control the depth to which the needle is inserted in the patient.

Accordingly, even without removing the cover 13 from the hub, but after removal from the container 14, a depth adjuster 15 can be fitted around the hub as shown in FIG. 2, which shows that a cylindrical end 19 of the adjuster extends beyond the hub towards the point of the needle and is spaced from it and effectively limits the extent to which the needle can be inserted in the patient. The adjuster has at the left hand end an external annular flange 33 leading to a cylindrical ring 22 which is a tight fit on a forwardly extending collar 23 moulded integrally with the hub.

Alternative adjusters 15 are provided with different lengths of the cylindrical portion 19 so that, by choosing the appropriate adjuster, and fitting it over the hub before the needle is inserted, the desired extent of insertion can be achieved without difficulty. FIG. 2 shows one adjuster in solid lines and an alternative adjuster in chain lines which would restrict the extent of penetration of the needle to 4 mm. The solid line adjuster 15 would allow penetration up to 8 mm.

After use, without having to remove the adjuster, the cover 13 can be replaced over the needle and fitted around the hub 12 so that the part of the needle that has been exposed is protected from causing contamination.

The container 14 has a seat 25 in its left hand face, for a closure (not shown) and has external ribs 26 for easy gripping and four internal circumferentially-spaced ribs 27 for gripping the hub 12.

The hub 12 is part of a moulding in the form of a cap which can be screwed onto the end of the syringe using a moulded internal thread 28 to cause the needle 11 to penetrate the closure of the container of the fluid that is to be injected. The cap can be gripped for that purpose by a number of external, circumferentially-spaced, axially-extending flutes, 29 which engage with the internal ribs 27 of the container 14 to provide a drive for assembling the needle assembly to the syringe. During fitting of the hub 12 on the container, the needle can be protected by the cover 13.

Each adjuster 15 is moulded with a number of internal, circumferentially-spaced ribs 31 for gripping the collar 23 on the hub.

What is claimed is:

1. A method of injecting a substance into a patient, the method comprising:
   (a) providing a needle combination including a needle for a syringe, a hub containing a boss carrying the needle, a depth adjuster and a cover which fits over the boss on the hub and defines an enclosure for the needle;
   (b) removably fitting the depth adjuster on the hub, so as to set the degree of penetration of the needle in the patient;
   (c) removing the cover;
   (d) inserting the needle into the patient; and
   (e) injecting the substance through the needle.

2. A method as claimed in claim 1 wherein the needle is a tight fit in the hub.

3. A method as claimed in claim 1 wherein the needle combination includes screw thread means for attaching the hub on the syringe.

4. A method as claimed in claim 1 wherein the depth adjuster is one of a number of alternative adjusters, each of which is of a different length from the others.

5. A method as claimed in claim 1 wherein the depth adjuster is in the form of a sleeve which is fitted to the hub and spaced around the needle.

* * * * *

UNITED STATES PATENT AND TRADEMARK OFFICE
CERTIFICATE OF CORRECTION

PATENT NO. : 5,015,235
DATED : May 14, 1991
INVENTOR(S) : David D. Crossman

It is certified that error appears in the above-identified patent and that said Letters Patent is hereby corrected as shown below:

In the title page, entry item [73], change the name of the Assignee from "National Carpet Equipment, Inc., Maple Grove, Minn." to -- Owen Mumford Ltd., Oxford, England. --

On the title page, the Attorney, Agent, or Firm, change "Haugen and Nikolai" to McAulay Fisher Nissen & Goldberg--.

Signed and Sealed this

Twenty-second Day of December, 1992

*Attest:*

DOUGLAS B. COMER

*Attesting Officer*   Acting Commissioner of Patents and Trademarks